US00PP07989P

United States Patent [19]

Fryer

[11] Patent Number: Plant 7,989

[45] Date of Patent: Sep. 29, 1992

[54] HYBRID TEA ROSE PLANT NAMED LIVERPOOL REMEMBERS

[75] Inventor: Gareth Fryer, Knutsford, England

[73] Assignee: Roses by Fred Edmunds, Inc., Wilsonville, Oreg.

[21] Appl. No.: 643,717

[22] Filed: Jan. 18, 1991

[51] Int. Cl.[5] ..... A01H 5/00

[52] U.S. Cl. ..... Plt./16

[58] Field of Search ..... Plt./11, 16, 17

*Primary Examiner*—Howard J. Locker

*Attorney, Agent, or Firm*—Christie, Parker & Hale

[57] ABSTRACT

A new hybrid tea rose with orange flowers.

1 Drawing Sheet

SUMMARY OF THE INVENTION

The present invention relates to a new and distinct variety of rose plant of the hybrid tea rose class which was originated by my crossing as seed parent the variety known as 'Corso' and as pollen parent an unnamed and unpatented seedling of my creation. The varietal denomination of this new rose is 'Liverpool Remembers'.

Among the novel characteristics possessed by this new variety which distinguishes it from its parents and all other varieties of which I am aware are its attractive well formed orange colored flowers borne on a plant particularly suitable for growing in outdoor gardens. Flowers open well and intensify in colorization as blooms age. Asexual reproduction by propagation by budding of the new variety as performed in Clackamas County, Oreg., shows that the foregoing and other distinguishing characteristics come true to form and are established and transmitted through succeeding propagations.

BRIEF DESCRIPTION OF ILLUSTRATION

The accompanying illustration show typical specimens of the vegetative growth and flowers of the new variety in different stages of development and depicted in color as nearly true as it is reasonably possible to make the same in a color illustration of this character.

DESCRIPTION OF THE NEW VARIETY

The new variety is an unusually fine hybrid tea rose with a color so bright it appears to have an inner glow. Since the color intensifies with age, old blooms need not be removed. The long pointed, medium sized buds have a silvery sheen on the petals reverse and are quite striking as well as ideal for cutting. The plant is very floriferous and almost always in bloom. Plants of the new variety are healthy and robust as well as resistant to common diseases.

The following is a detailed description of my new variety, with color terminology in accordance with the Royal Horticultural Society Colour Chart (R.H.S. Colour Chart). The terminology used in color description herein refers to plate numbers in the aforementioned color chart.

Parentage: Seedling.

*Seed parent.*—'Corso'.

*Pollen parent.*—Unnamed seedling.

Class: Hybrid tea.

The following information is from observations made of specimens grown indoors in Clackamas County, Oreg.

FLOWER

Blooming habit: Continuous.

A. Bud:

(1) *Size.*—Medium.

(2) *Form.*—Long pointed.

(3) *Color.*—As sepals divide, bud color is near 33C.

(4) *Sepals.*—Slightly longer than bud, single; glabrous outside and wooly on inside, especially at edges.

(5) *Penduncle.*—Length: Long. Aspect: Straight. Strength: Erect. Color: Near 146C.

Bloom:

(1) *Size.*—Average size when fully expanded — about 4 to 4½ inches.

(2) *Borne.*—Singly, usually with side buds.

(3) *Form.*—High centered at first, petals rolling outward, stamens evident in open bloom.

(4) *Petalage.*—Number of petals under normal conditions — about 25 to 30.

(5) *Color.*—After sepals fall and petals begin to unfurl, predominant color viewing petals undersurface of outer petal is near 29A to B. Petal top surface visible as flower opens is near 29A to 31A with darker orange hues seen on the outer petals and lighter hues on the inner petals, near 28C to D. Overall, tonality at a distance is near 29B to 31B. Color of petal of point of attachment is near 18A.

C. Petals:

(1) *Texture.*—Thick.

(2) *Appearance.*—Inside and outside satiny.

(3) *Form.*—Broad, fan shaped with some indentation or undulation at margin.

(4) *Arrangement.*—Regularly arranged, imbricated.

(5) *Petaloids in center.*—Few to none.

(6) *Persistence.*—Drop off cleanly.

(7) *Fragrance.*—Slight.

(8) *Lasting quality.*—Long lasting on plant and as cut flower.

REPRODUCTIVE ORGANS

A. Stamens, filaments and anthers:

*Arrangement.*—Regularly arranged around styles, irregular length, incurved.

*Color.*—Filaments near 55B, anthers near 13B.

B. Pollen.

*Color.*—Near 167A.

C. Styles: Short, uneven, but appear longer since carpels protrude even before fertilization.

D. Stigmas:

*Color.*—Stalk is near 61B, surface near 17B.

E. Hips: Truncate, globular, ½ to ¾ inch, carpels few (5-20), few hips set, near 153D at maturity, seeds protrude prominently.

PLANT

A. Form: Upright, slightly spreading.

B. Growth: Vigorous, H eight attained about 6 feet.

C. Foliage: Compound, 3 or 5 leaflets.

(1) *Size.*—Medium, slightly pendulous.

(2) *Quantity.*—Abundant.

(3) *Color.*—New foliage: Upper side — near 183A. Under side — near 183D. Old foliage: Upper side — near 139A. Under side — near 139B.

(4) *Shape.*—Long, acuminate.

(5) *Texture.*—Upper side is glossy; under side is matte.

(6) *Edge.*—Finely serrate.

(7) *Serration.*—Simple.

(8) *Leaf stem.*—Color — near 138B.

(9) *Stipules.*—Long, sometimes reaching over halfway up rachis to the first pair of leaflets, slightly bearded.

(10) *Resistance to disease.*—Mildew — Excellent. Blackspot — Excellent. Rust — Excellent.

D. Wood:

(1) *New wood.*—Color — near 183D. Bark — smooth, lustrous.

(2) *Old wood.*—Color — near 137B, waxy. Bark — smooth.

E. Thorns:

*Quantity (main stalk).*—Many, evenly distributed.

*On laterals from stalk.*—Few with many prickles.

*Form.*—Elongate, short base.

*Length.*—Long, narrow, nearly straight.

*Color.*—Near 60C (when young).

*Position.*—Regular on main stems, irregular on laterals.

*Prickles.*—Few on main stalks but profuse on laterals.

F. Winter hardiness: Needs protection in severe climates.

I claim:

1. A new and distinct variety of rose plant of the hybrid tea rose class, substantially as shown and described.

* * * * *

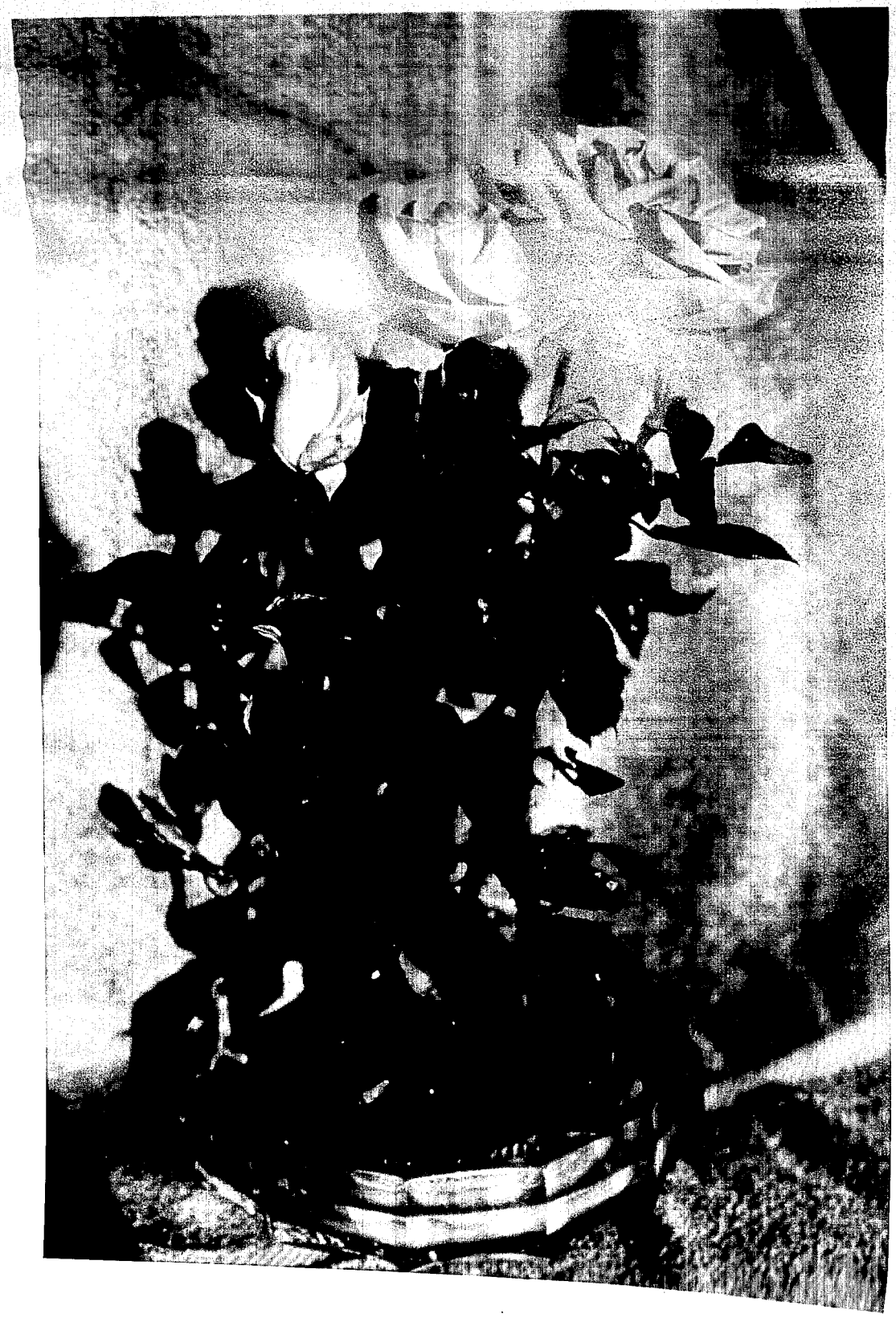

UNITED STATES PATENT AND TRADEMARK OFFICE

CERTIFICATE OF CORRECTION

PATENT NO. : Plant 7,989

DATED : September 29, 1992

INVENTOR(S) : Gareth Fryer

It is certified that error appears in the above-identified patent and that said Letters Patent is hereby corrected as shown below:

Column 1, lines 43,44, change "R.H.S. Colour Chart" to -- RHSCC --.

Column 3, line 9, change "(5-20)" to -- (15-20) --.
Column 3, line 15, change "H eight " to -- Height --.

Signed and Sealed this

Second Day of November, 1993

Bruce Lehman

*Attest:*

BRUCE LEHMAN

*Attesting Officer*

*Commissioner of Patents and Trademarks*